United States Patent [19]

Pauli et al.

[11] Patent Number: 5,436,950
[45] Date of Patent: Jul. 25, 1995

[54] FAN BEAM COMPUTED TOMOGRAPHY APPARATUS

[75] Inventors: Karlheinz Pauli, Neunkirchen; Helmut Winkelmann, Forchheim, both of Germany

[73] Assignee: Siemens Aktiengesellschaft, Munich, Germany

[21] Appl. No.: 309,881

[22] Filed: Sep. 20, 1994

[30] Foreign Application Priority Data

Oct. 15, 1993 [DE] Germany ............. 43 35 300.2

[51] Int. Cl.$^6$ ............................................. G06F 15/42
[52] U.S. Cl. ............................ 378/4; 378/205; 378/137
[58] Field of Search .......... 378/4, 12, 15, 19, 20, 378/137, 138, 205

[56] References Cited

U.S. PATENT DOCUMENTS

| | | | |
|---|---|---|---|
| 4,703,424 | 10/1987 | Gullberg et al. | 364/414 |
| 4,812,983 | 3/1989 | Gullberg et al. | 364/413.17 |
| 4,979,199 | 12/1990 | Cueman et al. | 378/138 |

FOREIGN PATENT DOCUMENTS

1584954 2/1981 United Kingdom .

OTHER PUBLICATIONS

"Patents Abstracts of Japan," P-1285, vol. 15, No. 483, Dec. 6, 1991, Application No. 2-4256.

*Primary Examiner*—David P. Porta
*Assistant Examiner*—Don Wong
*Attorney, Agent, or Firm*—Hill, Steadman & Simpson

[57] ABSTRACT

A computed tomography has a frame carrying an x-ray source and an x-ray detector which are rotated by the frame around an examination subject to obtain a series of exposures from different angular positions. The x-ray source emits a fan beam from a focus and includes a focus deflecting unit for adjusting the position of the focus in the event that, due to mechanical wear or play, the frame is caused to rotate around a point which differs from the intended rotational center. The intended rotational center is a point through which a straight line extending between the focus and the center of the radiation detector always proceeds for every angular position. Two sensors are disposed on the rotating center frame in addition to the x-ray source and the radiation detector, these two sensors respectively defining two measuring points and supplying output signals corresponding to the respective positions of these measuring points relative to a reference point on a stationary part of the apparatus. The output signals are supplied to correction electronics, which also receives an output signal from a focus control unit, and effects a deflection of the focus by means of the focus deflecting unit as needed to maintain rotation of the frame around the intended rotational center.

1 Claim, 3 Drawing Sheets

FAN BEAM COMPUTED TOMOGRAPHY APPARATUS

BACKGROUND OF THE INVENTION

1. Field of the Invention

The present invention is directed to a computed tomography apparatus of the type wherein an x-ray fan beam is caused to be rotated around an examination subject to irradiate the subject from a series of different angular positions.

2. Description of the Prior Art

In computed tomography systems of the type generally described above, the x-ray source which emits the fan beam, and the x-ray detector, are rotated around a rotational center on a rotating frame. The rotational center and the center of gravity of the focus of the focal spot of the x-ray tube should lie on a straight line for all angular positions. If, due to mechanical wear or play, the rotational center changes in position, the system is out of adjustment.

In a system which is out of adjustment, the fan beam geometry no longer corresponds to the theoretical geometry which is used in the image computation, and thus results in a loss of image sharpness and a degradation of the modulation transfer function (MTF).

Rotational bearings having extremely tight tolerances are consequently required in a computed tomography apparatus. The position of the fan beam must be readjusted in the event of a change in the position of the rotational center of the bearing. Moreover, the bearing must be replaced if it exhibits a constant, drift-like variation in the position of the rotational center, since the constant readjustment which is necessary under such conditions has a highly limiting effect on the use of the system.

A computed tomography system is described Patent Abstracts of Japan, P-1285, Dec. 6, 1991, Vol. 15/No. 483 having an x-ray source which irradiates a specimen, with the specimen being rotated around a rotational center. The x-ray source, the rotational center of the specimen, and the center of the x-ray detector in this known apparatus always lie on the same connecting straight line. This computed tomography apparatus, however, is not suitable for examination of patients for medical purposes, since medical computed tomography systems do not rotate the patient.

A computed tomography apparatus is disclosed in United Kingdom application 15 84 954 having means for deflecting the focus of the x-ray tube. The focus deflection, however, is not for the purpose of compensating undesired dislocations of the rotational center. Instead, the focus displacement in this known system ensues for the purpose of improving the image. A computed tomography apparatus is disclosed in German OS 35 46 233 wherein a correction of displacements of the rotational center ensues by computation.

SUMMARY OF THE INVENTION

It is an object of the present invention to provide a computed tomography apparatus of the type wherein a fan beam is rotated around a subject on a rotating frame which rotates around a rotational center, wherein any change in the position of the rotational center is measured and is compensated by adjusting the position of the beam focus.

The above object is achieved in accordance with the principles of the present invention in a computed tomography apparatus wherein two sensors are disposed on the rotating frame in addition to the x-ray source and the x-ray detector, the two sensors defining two measuring points and supplying respective output signals corresponding to the position of these measuring points, relative to a reference point on a stationary part, to correction electronics. The correction electronics also receives an output signal from a focus control unit, and effects deflection of the focus by means of a focused deflecting unit dependent on the received signals.

The adjustment of the position of the focus in the computed tomography apparatus of the invention ensues automatically, with the displacement of the focus position being accomplished magnetically, mechanically or electrically. When the positional change of the rotational center is measured relative to a line which is normal (perpendicular) to a straight connecting line between the x-ray source and the center of the x-ray detector, the measured deviation in this direction can be compensated by deflecting the focus so that the focus, the rotational center and the detector center again lie on a straight line. Displacement of the rotational center along this straight connecting line is thereby negligible. The measurement of the position of the rotational center ensues as soon as the gantry (frame) rotates together with the x-ray source and the x-ray detector. The correction signal is continuously calculated and is supplied to the focus deflection unit. The measured result is held at a most recent value during the actual time of the image exposure, in order to avoid any variations in position occurring during the exposure, which would affect the image quality.

DESCRIPTION OF THE PREFERRED EMBODIMENTS

Figure 1:
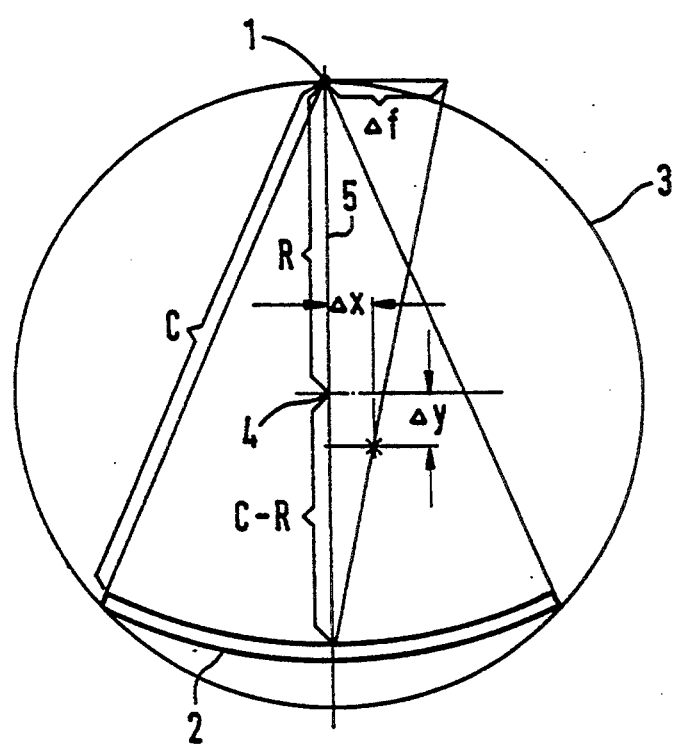
FIG. 1 is a schematic illustration for explaining the geometry of a computed tomography apparatus employing a rotating fan beam, for explaining the concept of the invention.

In the geometrical representation of a computed tomography apparatus illustrated in FIG. 1, the position of the focus is referenced 1, from which an x-ray fan beam emanates which is incident on an x-ray detector 2. The focus 1 rotates together with the detector 2 on a circle 3 around a rotational center 4. As a result, an examination subject (not shown) is transirradiated with x-rays from different angular directions. A computer calculates an image of the examination subject from the output signals of the detector 2, and this image can be reproduced on a monitor.

If the rotational center 4 changes its position by $\Delta x$, $\Delta y$, the system is out of adjustment. FIG. 1 shows that the focus 1 must be shifted by an amount $\Delta f$ in the fan direction in order to restore the original adjustment, whereby $$\Delta f = \Delta x \frac{C}{C - R - \Delta y}$$

applies, with C being a segment extending between the focus 1 and an extreme, outer edge of the x-ray detector 2, and R being the radius of the circle 3.

Because the radial component $\Delta y$ is small in comparison to R and C, it can be left out of consideration (for $\Delta y = 1$ mm, the error amounts to $6 \cdot 10^{-3}$).

Because the radial component $\Delta y$ of the positional change of the rotational center 4 can be left out of consideration, measuring the components $\Delta x$ perpendicular to the straight connecting line 5 between the focus 1 and the center of the detector 2 is sufficient.

Two measuring points carried by the rotatable part of the computed tomography apparatus at opposite sides of the fan beam, and at least one reference point on the stationary part of the computed tomography apparatus are required for measuring $\Delta x$.

Figure 2:
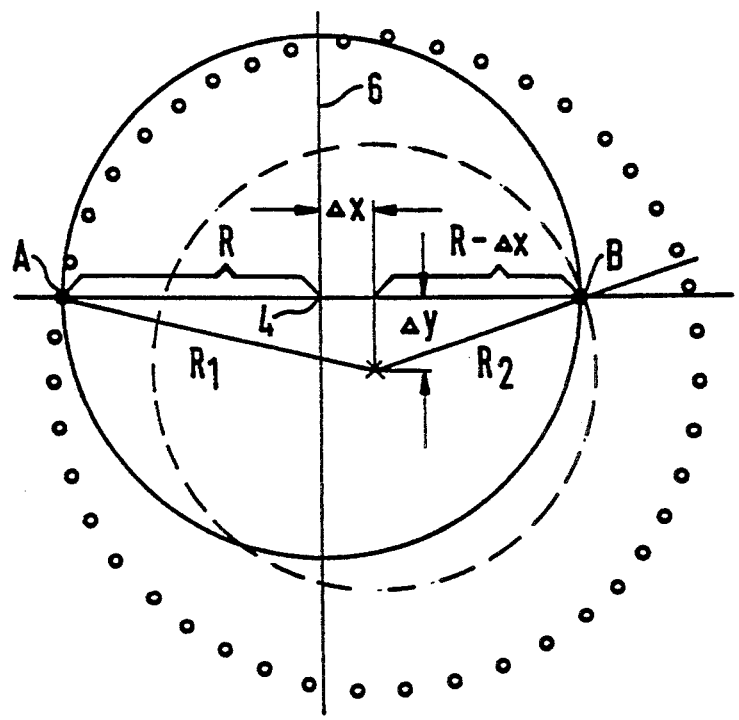
FIGS. 2 and 3 are schematic illustrations for explaining the acquisition of the displacement of the rotational center in accordance with the principles of the present invention.

FIG. 2 illustrates the case wherein the two measuring points A and B are disposed on a straight line which runs through the rotational center 4, the measuring points A and B being disposed symmetrically relative to the fan axis 6 at the distance R from the rotational center 4. When the rotational center 4 is displaces by $\Delta x$, $\Delta y$, the measuring points A and B then move on concentric circles having respective radii $R_1$ and $R_2$, according to the following equations:

$$R_1 = \sqrt{\Delta y^2 + \Delta x^2 + R^2 + 2\Delta x R}.$$

$$R_2 = \sqrt{\Delta y^2 + \Delta x^2 + R^2 - 2\Delta x R}.$$

The relationship $R_1 - R_2 = 2\Delta x$ is valid for $\Delta y = 0$. This relationship is also valid for all values of $\Delta y$ which occur in practice, since $\Delta y^2$ is always small in comparison to $R^2$. The value $\Delta y$ can therefore be left out of consideration.

Figure 3:
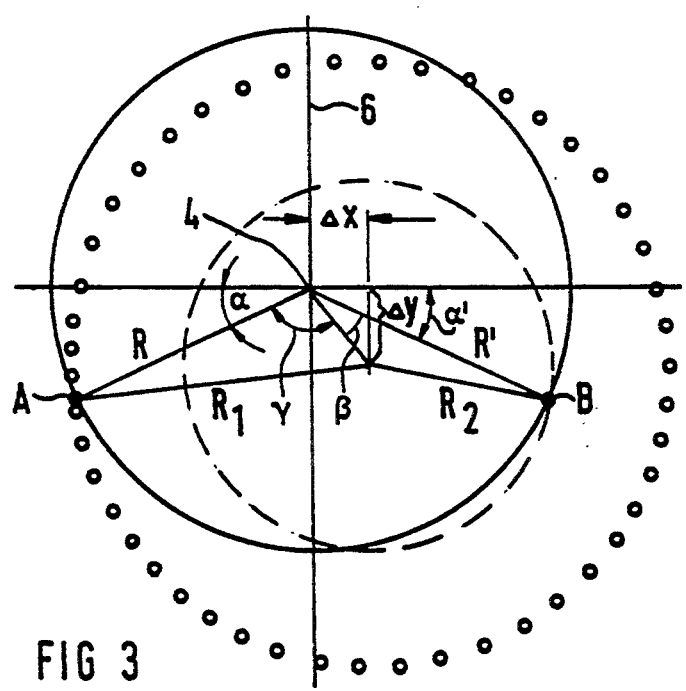

FIG. 3 illustrates the general case wherein the specific arrangement of the measuring points A and B shown in FIG. 2 cannot be employed. The measuring points A and B in the illustration of FIG. 3 lie at arbitrary angles relative to the focus and the detector 2, and the respective distances of the measuring points A and B from the rotational center 4 are unequal. Because $R \neq R'$, the measuring points A and, B for $\Delta x = 0$ and $\Delta y = 0$ also move on concentric circles having different diameters. The change in the difference of the radii is a criterion for $\Delta x$.

$$\Delta x = \frac{1}{2}[(R - R') - (R_1 - R_2)]$$

The following expressions are valid for $R_1$ and $R_2$:

$$R_1 = \sqrt{\Delta x^2 + \Delta y^2 + R^2 - 2\sqrt{\Delta x^2 + \Delta y^2} R \cos \gamma}$$

$$R_2 = \sqrt{\Delta x^2 + \Delta y^2 + R'^2 - 2\sqrt{\Delta x^2 + \Delta y^2} R' \cos \gamma}$$

wherein in $\gamma$ is the angle indicated in FIG. 3 as the supplement of angles $\alpha$, $\alpha'$ and $\beta$, with $\alpha$ being the angle made by R with a horizontal diameter passing through the rotational center 4, $\alpha'$ being the angle made by R' with the aforementioned horizontal diameter, and $\alpha'$ and $\beta$ comprising the angle defined by the end point of $\Delta y$ with the aforementioned horizontal diameter.

Because the two measurement points A and B rotate on concentric circles, one reference point at the stationary apparatus part in an arbitrary angular range suffices for calculating $\Delta x$, assuming that the radii R and R' differ only slightly.

The demands made on the mechanical systems (bearings) can be reduced in a computed tomography apparatus employing the above-described technique for focus adjustment. Complicated calculating which take the position of the rotational center into consideration in the image pick-up system, or in the image reconstruction calculations, are eliminated.

Figure 4:
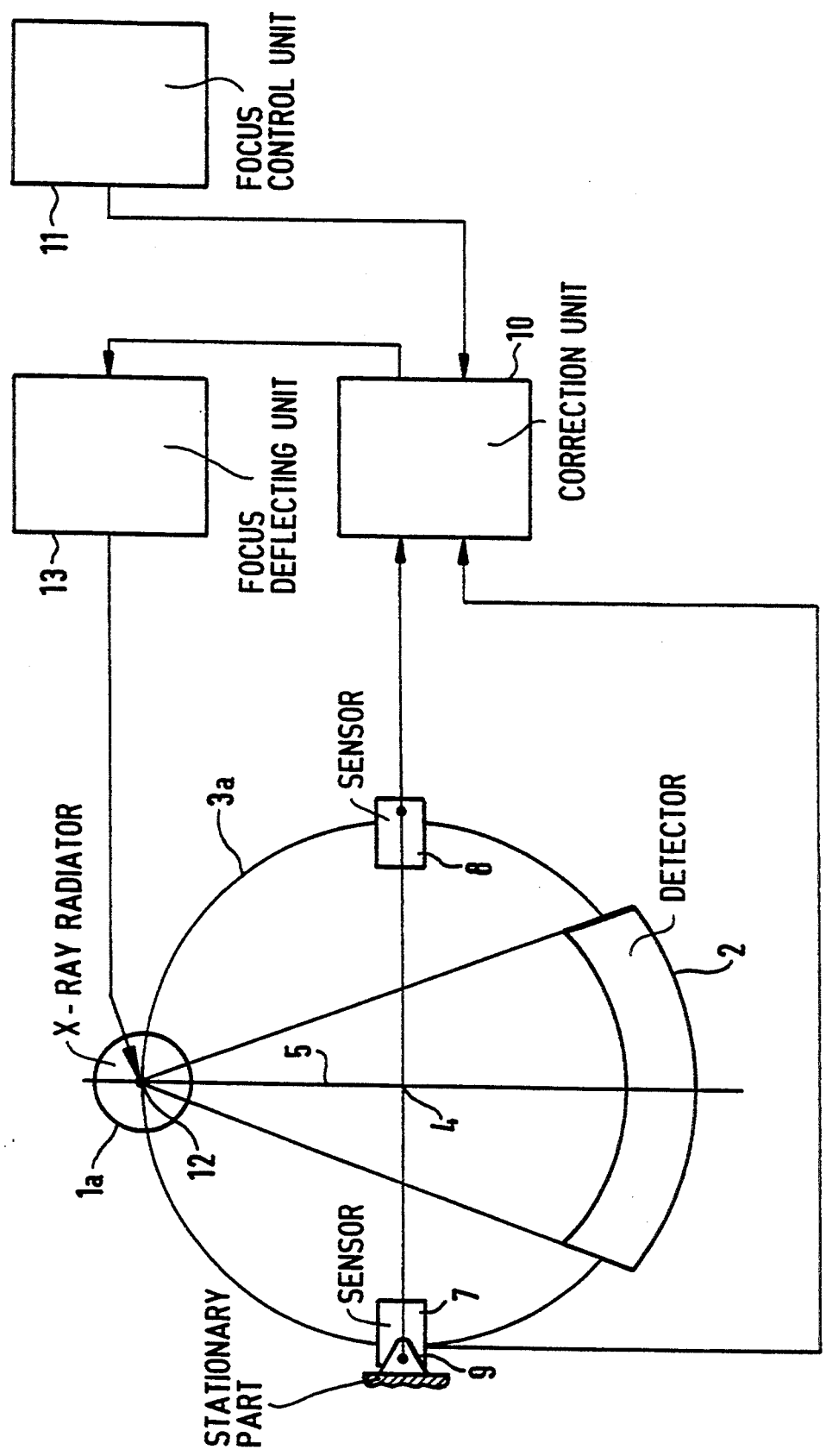
FIG. 4 is a schematic blocked diagram of a computed tomography apparatus constructed and operating in accordance with the principles of the present invention.

The relevant components of a computed tomography system embodying the above-described focused deflection are shown in FIG. 4. The system includes an x-ray radiation 1a, having a focus 12 from which an x-ray fan beam emanates. The fan beam is incident on a detector 2. The x-ray radiator 1a and the detector 2 are rotated around the rotational center 4 on a rotating frame 3a. Two sensors 7 and 8, corresponding to the aforementioned measuring points A and B, are also mounted on the rotating frame 3a of the computed tomography apparatus, and rotate on the frame 3a together with the radiator 1a and the detector 2. A stationary part of the apparatus is schematically indicated, at which a stationary reference point 9 is disposed. The output signals of the sensors 7 and 8 are supplied to a correction unit 10, which also receives an output signal from a focus control unit 11. The correction unit 10 generates a correction signal from its input signals, which is supplied to a focus deflecting unit 13. The focus deflecting unit 13 causes the focus 12 to be changed in position, dependent on the signals from the sensors 7 and 8, so that a straight connecting line between the focus 12 and the center of the detector 2 always proceeds through the rotational center 4, for every angular position.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computed tomography apparatus comprising:

an x-ray source having a focus from which an x-ray fan beam emanates;

a rotating frame on which said x-ray source is mounted;

an x-ray detector mounted on said frame opposite said x-ray source, said rotating frame rotating said x-ray source and said detector around a rotational center;

means for deflecting a position of said focus;

a stationary apparatus part having a reference point thereon;

two sensors disposed on said frame and rotating with said frame around said rotational center, said sensors respectively defining two measuring points and generating output electrical signals corresponding to the position of said two measuring points with respect to said reference point on said stationary apparatus part;

a focus control unit; and correction means, supplied with said output electrical signals from said two sensors and with an output signal from said focus control unit, for generating a control signal for operating said means for deflecting said focus for maintaining a straight connecting line extending between said focus and a center of said detector to always proceed through said rotational center.

* * * * *